US010398567B2

(12) United States Patent
Robinson

(10) Patent No.: US 10,398,567 B2
(45) Date of Patent: Sep. 3, 2019

(54) EXPANDABLE, ADJUSTABLE INTER-BODY FUSION DEVICES AND METHODS

(71) Applicant: SPECTRUM SPINE IP HOLDINGS, LLC, Atlanta, GA (US)

(72) Inventor: James C. Robinson, Atlanta, GA (US)

(73) Assignee: SPECTRUM SPINE IP HOLDINGS, LLC, Atlanta, GA (US)

( * ) Notice: Subject to any disclaimer, the term of this patent is extended or adjusted under 35 U.S.C. 154(b) by 0 days.

(21) Appl. No.: 15/766,483

(22) PCT Filed: Oct. 11, 2016

(86) PCT No.: PCT/US2016/056475
§ 371 (c)(1),
(2) Date: Apr. 6, 2018

(87) PCT Pub. No.: WO2017/062993
PCT Pub. Date: Apr. 13, 2017

(65) Prior Publication Data
US 2018/0289499 A1    Oct. 11, 2018

Related U.S. Application Data

(60) Provisional application No. 62/239,448, filed on Oct. 9, 2015.

(51) Int. Cl.
*A61F 2/44*       (2006.01)
*A61F 2/46*       (2006.01)
*A61F 2/30*       (2006.01)

(52) U.S. Cl.
CPC .......... *A61F 2/447* (2013.01); *A61F 2/4455* (2013.01); *A61F 2/4684* (2013.01);
(Continued)

(58) Field of Classification Search
CPC ................. A61F 2/447; A61F 2/4684; A61F 2002/30383; A61F 2002/30482;
(Continued)

(56) References Cited

U.S. PATENT DOCUMENTS 6,375,683 B1 *  4/2002  Crozet .................... A61F 2/44
                                                         623/17.15
8,496,706 B2 *  7/2013  Ragab .................... A61F 2/447
                                                         623/17.11
(Continued)

FOREIGN PATENT DOCUMENTS

DE    102012023042    11/2013
FR        2762778     11/1998
(Continued)

OTHER PUBLICATIONS

Extended European Search Report issued for corresponding European Application No. 16854572.1 dated Apr. 15, 2019.

*Primary Examiner* — Pedro Philogene
*Assistant Examiner* — David C Comstock
(74) *Attorney, Agent, or Firm* — FisherBroyles LLP; Anthony J DoVale

(57) ABSTRACT

An expandable, adjustable inter-body fusion device is presented. The inter-body fusion device can have a first plate, a second plate, and an insert positioned substantially therebetween the first plate and the second plate. The first plate, the second plate, and the insert define an interior cavity. Rotation of the insert relative to the first and second plates increases or decreases the distance of the first plate with respect to the second plate, effectively expanding the inter-body fusion device and increasing the volume of the interior cavity. The angle between the first plate and the second plate is selectively adjustable.

21 Claims, 14 Drawing Sheets

(52) U.S. Cl.
CPC ............... *A61F 2002/30383* (2013.01); *A61F 2002/30482* (2013.01); *A61F 2002/30515* (2013.01); *A61F 2002/30538* (2013.01); *A61F 2002/30556* (2013.01); *A61F 2002/30579* (2013.01); *A61F 2002/4625* (2013.01); *A61F 2002/4627* (2013.01)

(58) Field of Classification Search
CPC .. A61F 2002/30515; A61F 2002/30538; A61F 2002/30556
USPC ............................................ 623/17.15, 17.16
See application file for complete search history.

(56) References Cited

U.S. PATENT DOCUMENTS

| | | | | |
|---|---|---|---|---|
| 9,078,767 | B1* | 7/2015 | McLean | A61F 2/4455 |
| 2002/0052656 | A1* | 5/2002 | Michelson | A61F 2/4455 |
| | | | | 623/17.11 |
| 2002/0072801 | A1* | 6/2002 | Michelson | A61F 2/4455 |
| | | | | 623/17.11 |
| 2002/0177897 | A1 | 11/2002 | Michelson | |
| 2005/0234555 | A1* | 10/2005 | Sutton | A61F 2/442 |
| | | | | 623/17.15 |
| 2006/0241621 | A1* | 10/2006 | Moskowitz | A61B 17/0642 |
| | | | | 623/17.11 |
| 2012/0029637 | A1* | 2/2012 | Ragab | A61F 2/447 |
| | | | | 623/17.11 |
| 2013/0197642 | A1 | 8/2013 | Ernst | |
| 2013/0211525 | A1* | 8/2013 | McLuen | A61F 2/4455 |
| | | | | 623/17.16 |
| 2014/0277473 | A1* | 9/2014 | Perrow | A61F 2/447 |
| | | | | 623/17.15 |
| 2016/0135960 | A1* | 5/2016 | Grotz | A61F 2/4637 |
| | | | | 623/17.16 |

FOREIGN PATENT DOCUMENTS

| | | |
|---|---|---|
| WO | 2010078520 A8 | 7/2010 |
| WO | 2015063721 A1 | 5/2015 |

* cited by examiner

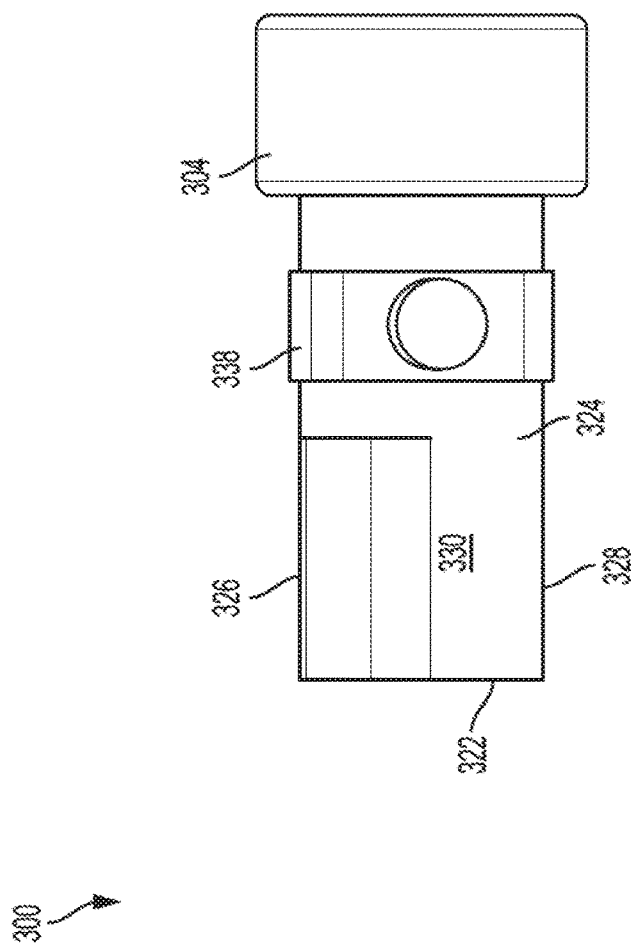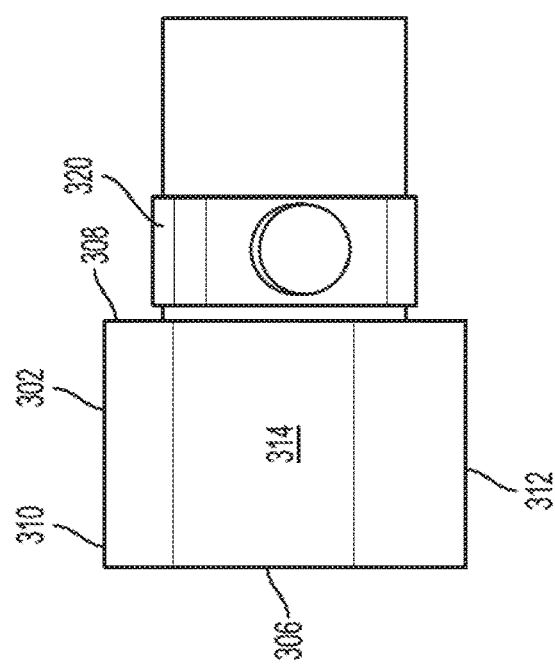
FIG. 6

EXPANDABLE, ADJUSTABLE INTER-BODY FUSION DEVICES AND METHODS

CROSS-REFERENCE TO RELATED PATENT APPLICATIONS

This application is a national stage under 35 U.S.C. 371 based on and claiming the benefit of International Application No. PCT/US2016/056475, filed on Oct. 11, 2016, which claims the benefit of U.S. Provisional Application No. 62/239,448, filed on Oct. 9, 2015, which is incorporated by reference herein in its entirety.

FIELD OF THE INVENTION

This invention relates generally to spinal surgery, and more particularly to devices and methods for stabilization of the spine in association with placement of an expandable inter-body construct with an adjustable construct angle for inter-body fusion or the like.

BACKGROUND OF THE INVENTION

Damage or disease that affects the spinal disc within an individual's spinal column may lead to neurologic impairment with possible permanent damage to the surrounding tissue. Maintaining proper anatomic spacing and lordosis within the spine is critical to ensuring continued functionality of the surrounding tissue and for the spinal column, the spinal cord and nerve roots and therefore, avoidance of long term serious neurological impairment.

Typically, spinal implants that are used as a spacer type of device have a fixed overall length and are implanted without the ability to adjust the degree of expansion or curvature without using multiple insertion instrumentation. Some of the known procedures for introducing spinal implants comprise Anterior Lumbar Inter-body Fusion ("ALIF"), Lateral Lumbar Inter-body Fusion ("LLIF"), Posterior Lumbar Inter-body Fusion ("PLIF"), Oblique Lumbar Inter-body Fusion ("OLIF"), Direct Lateral Fusion ("DLIF"), Transforaminal Lumbar Interbody Fusion ("TLIF"), and the like. A need remains for an expandable, adjustable spacer type of implant that allows the surgeon to insert the implant in an unexpanded position to minimize the size of the surgical incision, facilitate the operative technique and decrease patient morbidity.

SUMMARY

Presented herein is an inter-body fusion device, or implant, for use in spinal surgery. In one aspect, the inter-body fusion device can be an expandable fusion device having an expandable height and volume. In another aspect, the inter-body fusion device can be an adjustable fusion device such that an angle formed between an upper bone contact surface and a lower bone contact surface is selectively adjustable by the surgeon.

In one aspect, the inter-body fusion device comprises a first plate, a second plate, and an insert positioned substantially therebetween the first plate and the second plate. The first plate, the second plate, and the insert define an interior cavity. In one aspect, rotating at least a portion of the insert relative to the first and second plates in a first direction increases the distance between the first plate relative to the second plate, effectively expanding the inter-body fusion device and increasing the volume of the interior cavity. In another aspect, rotating at least a portion of the insert relative to the first and second plates in the first direction increases the angle formed between the first plate relative to the second plate.

It is contemplated that this technology can be used for a variety of implants used for a variety of spinal procedures. These procedures include, but are not limited to OLIF (anterior or posterior), DLIF, PLIF, TLIF, ALIF, and LLIF. So, depending upon the procedure and point of insertion for the implant, the geometry of the implant can differ.

In an exemplified aspect, at least one of the first plate and the second plate define at least one graft window that is in communication with the interior cavity.

Also presented herein are methods of using an inter-body fusion device during an inter-body fusion procedure. In one aspect, the method comprises accessing the desired disc space, choosing the correct insert size with the appropriate height range, inserting the inter-body fusion device into the desired area in the disc space, expanding the inter-body fusion device from a first unexpanded position to a second expanded position and adjusting the angle formed between the first plate relative to the second plate to a desired angle. An additional step of packing the interior cavity via with bone fusion material either prior to or after expansion is also contemplated.

Related methods of operation are also provided. Other apparatuses, methods, systems, features, and advantages of the inter-body fusion device and the method of its use will be or become apparent to one with skill in the art upon examination of the following figures and detailed description. It is intended that all such additional apparatuses, methods, systems, features, and advantages be included within this description, be within the scope of the inter-body fusion device and the method of its use, and be protected by the accompanying claims.

DESCRIPTION OF THE FIGURES

The accompanying drawings, which are incorporated in and constitute a part of this specification, illustrate certain aspects of the instant invention and together with the description, serve to explain, without limitation, the principles of the invention. Like reference characters used therein indicate like parts throughout the several drawings.

FIG. 6 is a side elevational view of the insert of FIG. 5;

DESCRIPTION OF THE INVENTION

Figure 1:
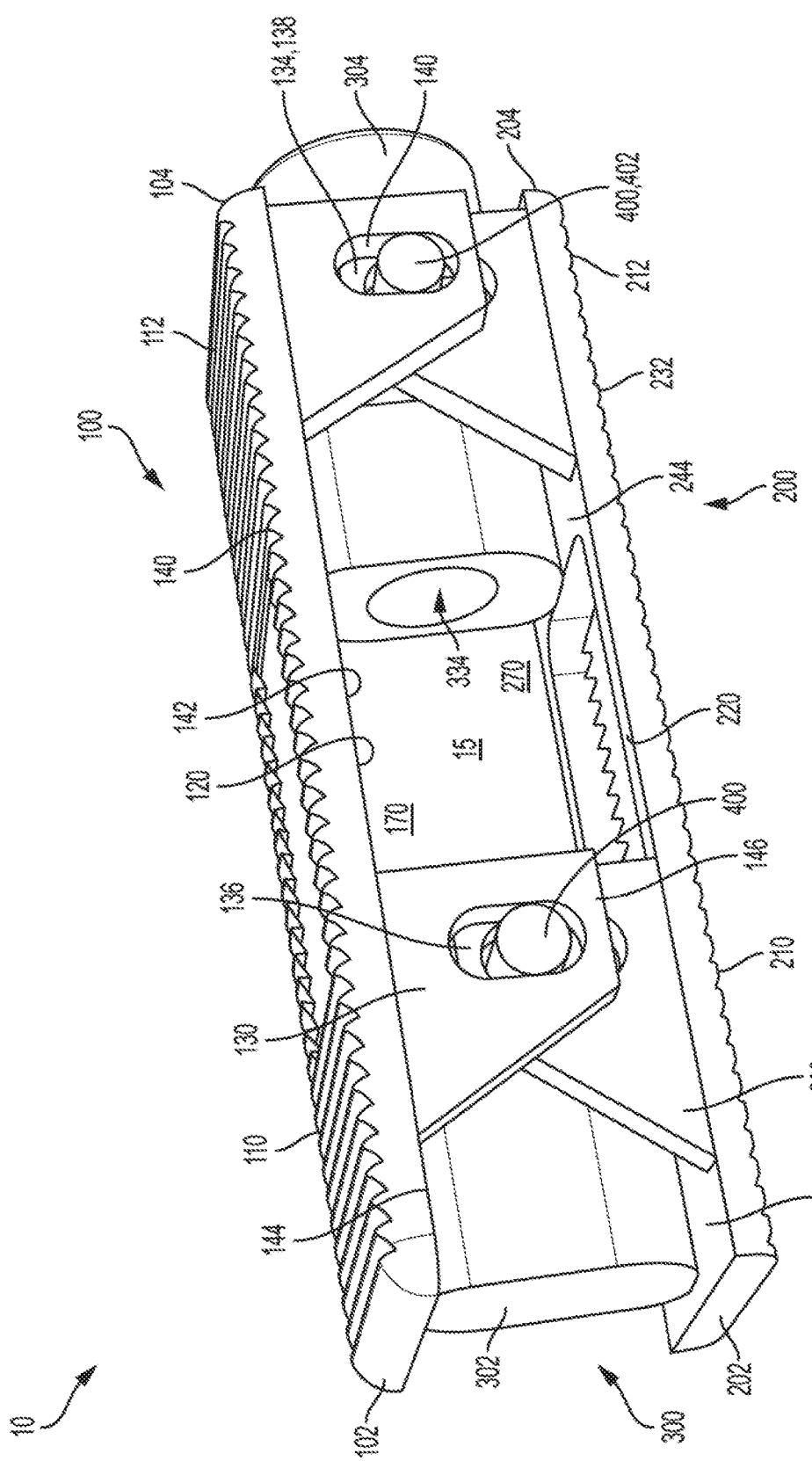
FIG. 1 is a front perspective view of one embodiment of an expandable, adjustable inter-body fusion device in a second expanded position, the device comprising a first plate, a second plate and an insert, according to one aspect.
Figure 2:
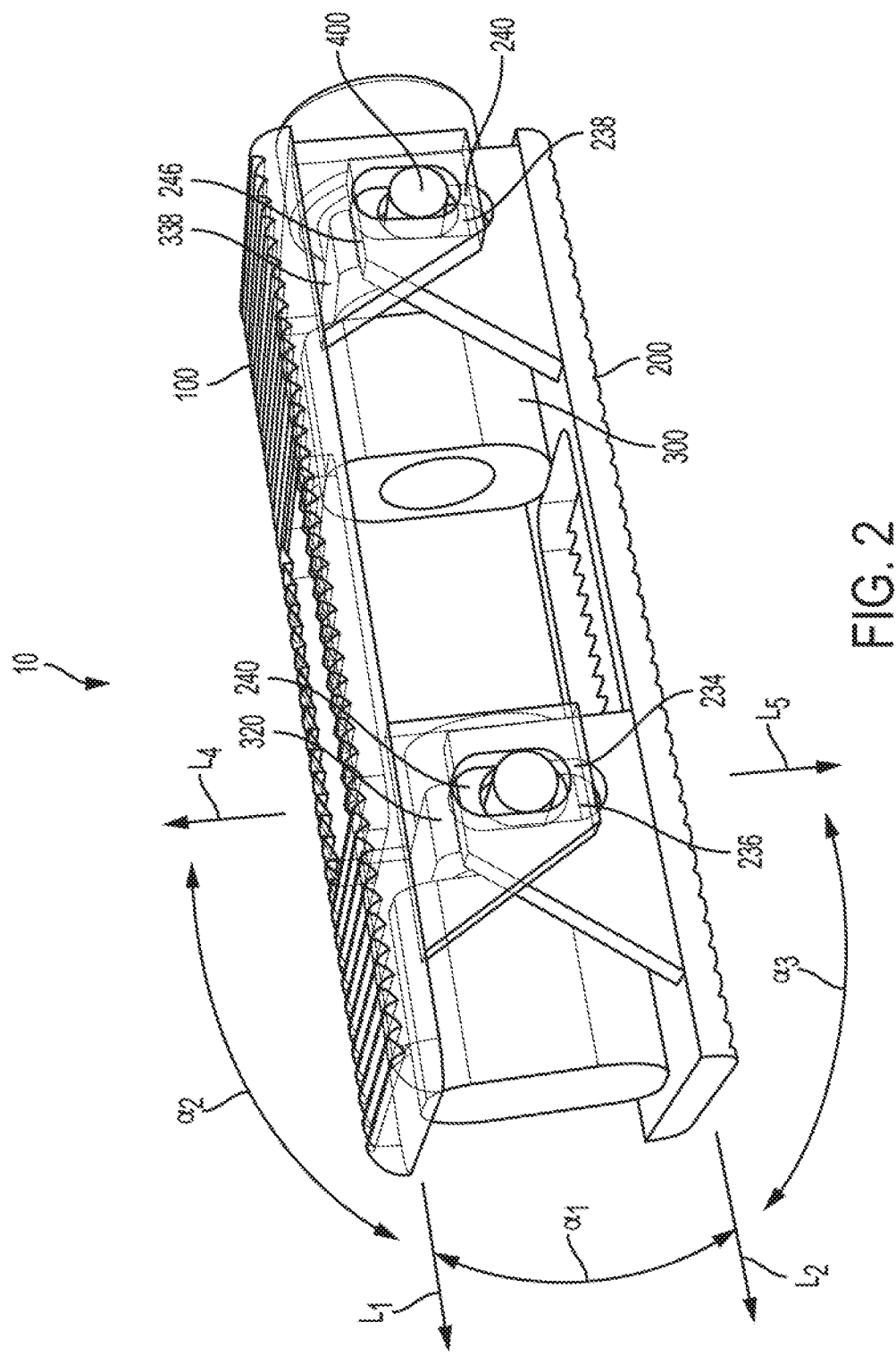
FIG. 2 is a front perspective of the inter-body fusion device of FIG. 1 in the second expanded position, in which a device angle between the first plate and the second plate is substantially 0 degrees (the first plate and the second plate are substantially parallel), and in which the first plate is illustrated transparently for clarity.
Figure 3:
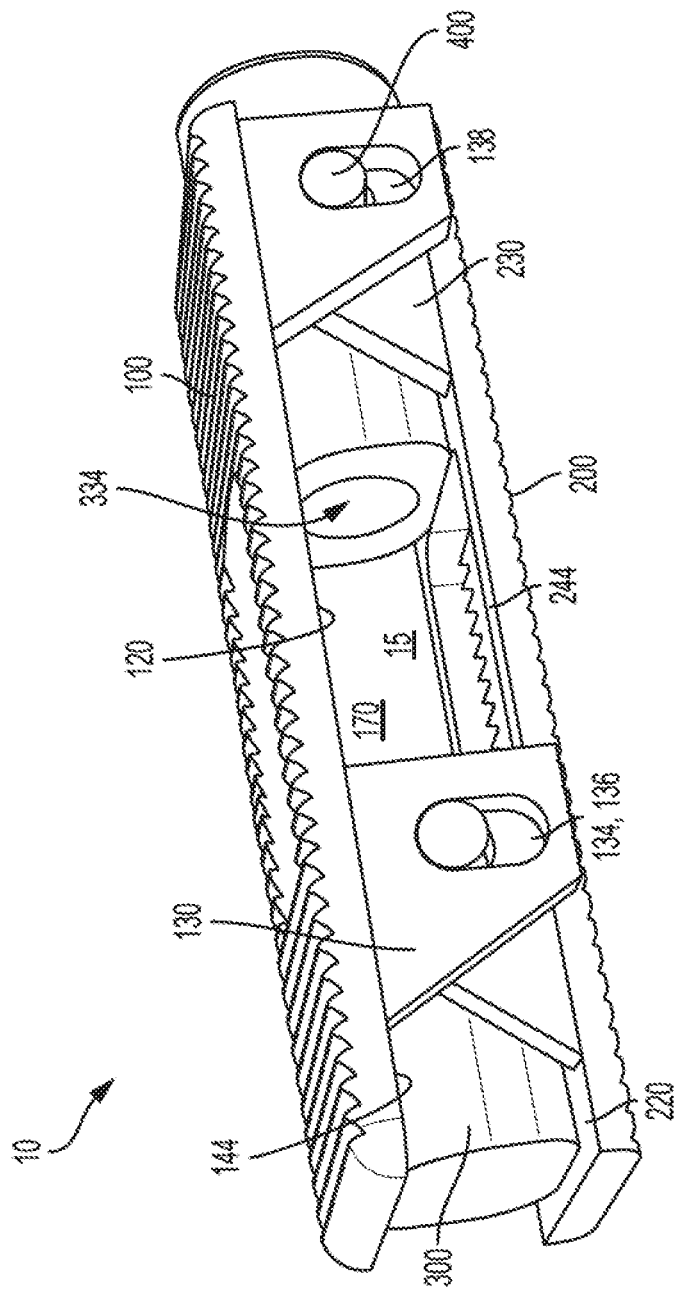
FIG. 3 is a front perspective of the inter-body fusion device of FIG. 1 in a first unexpanded position.
Figure 4:
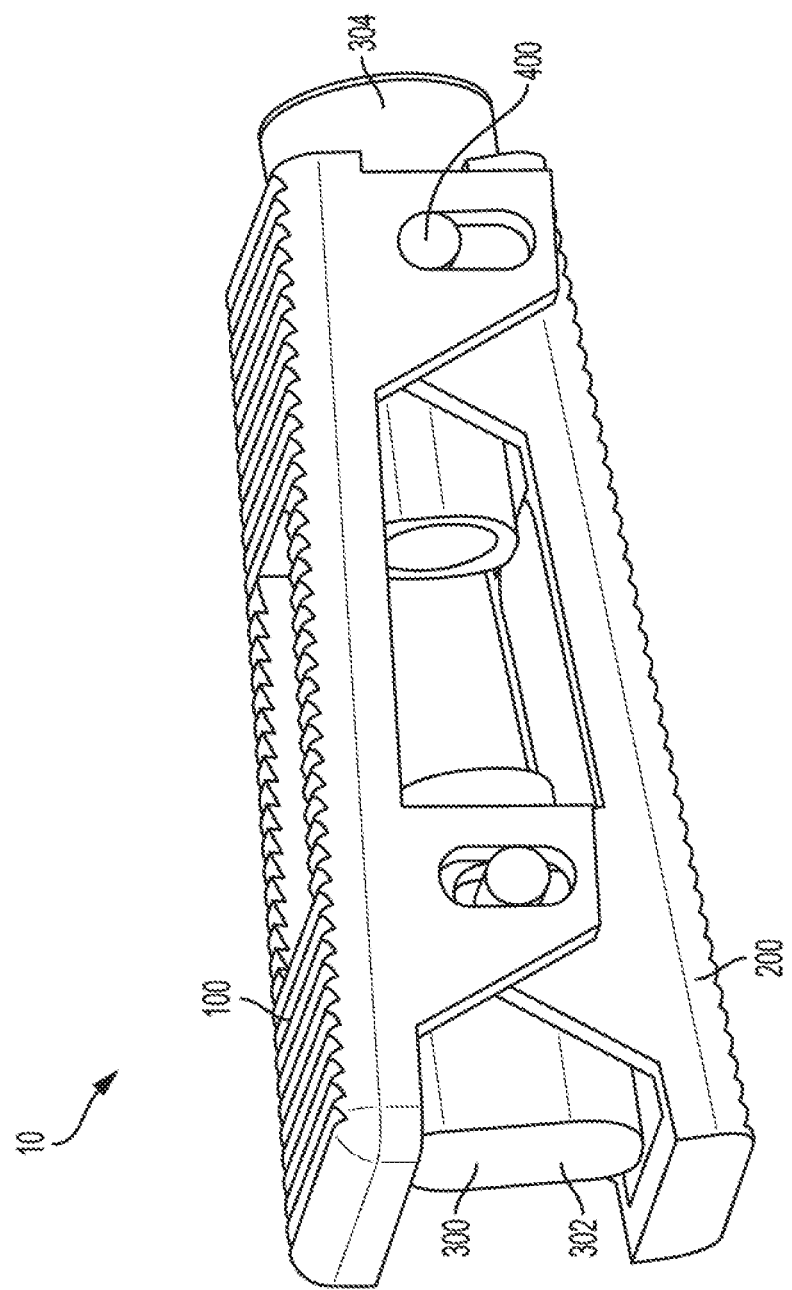
FIG. 4 is a front perspective of the inter-body fusion device of FIG. 1 in the second expanded position, and in which the device angle between the first plate and the second plate is greater than 0 degrees.
Figure 5:
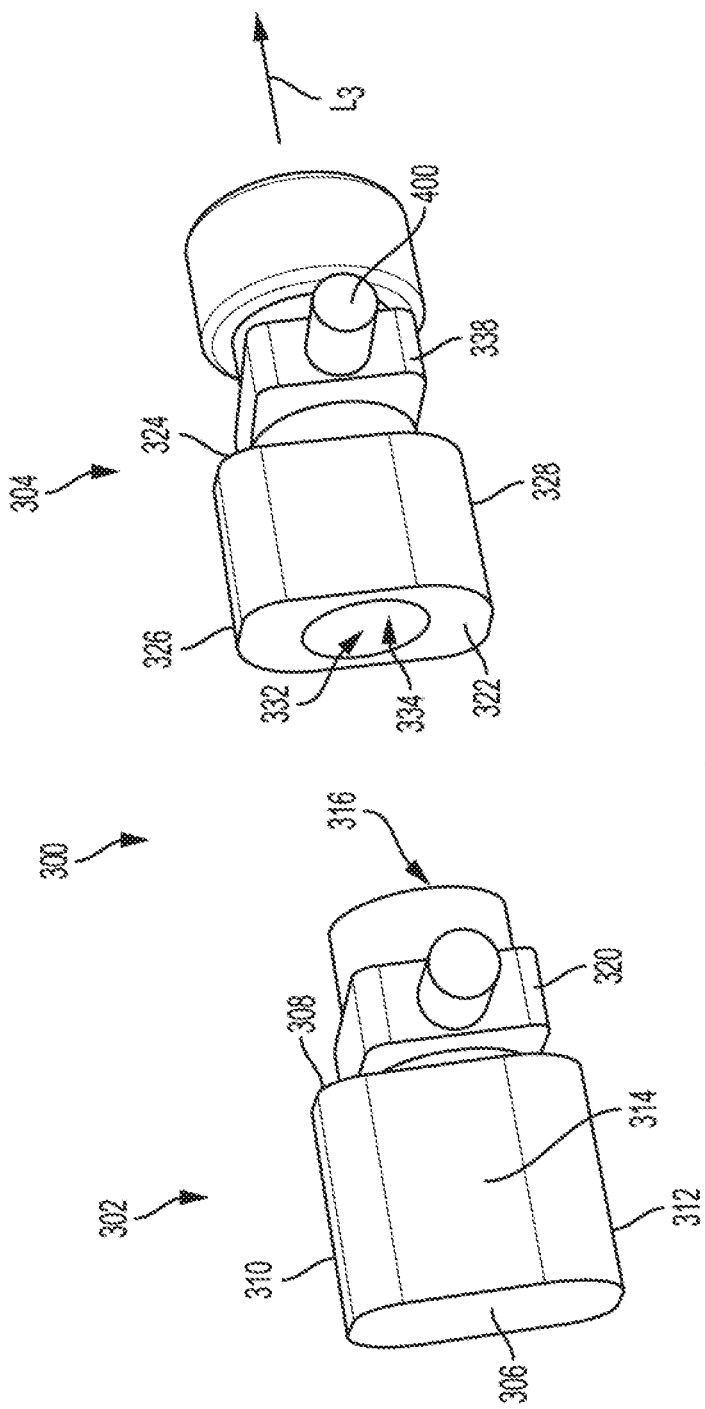
FIG. 5 is front perspective view of the insert of FIG. 1, the insert comprising a first member and a second member, according to one aspect.
Figure 7:
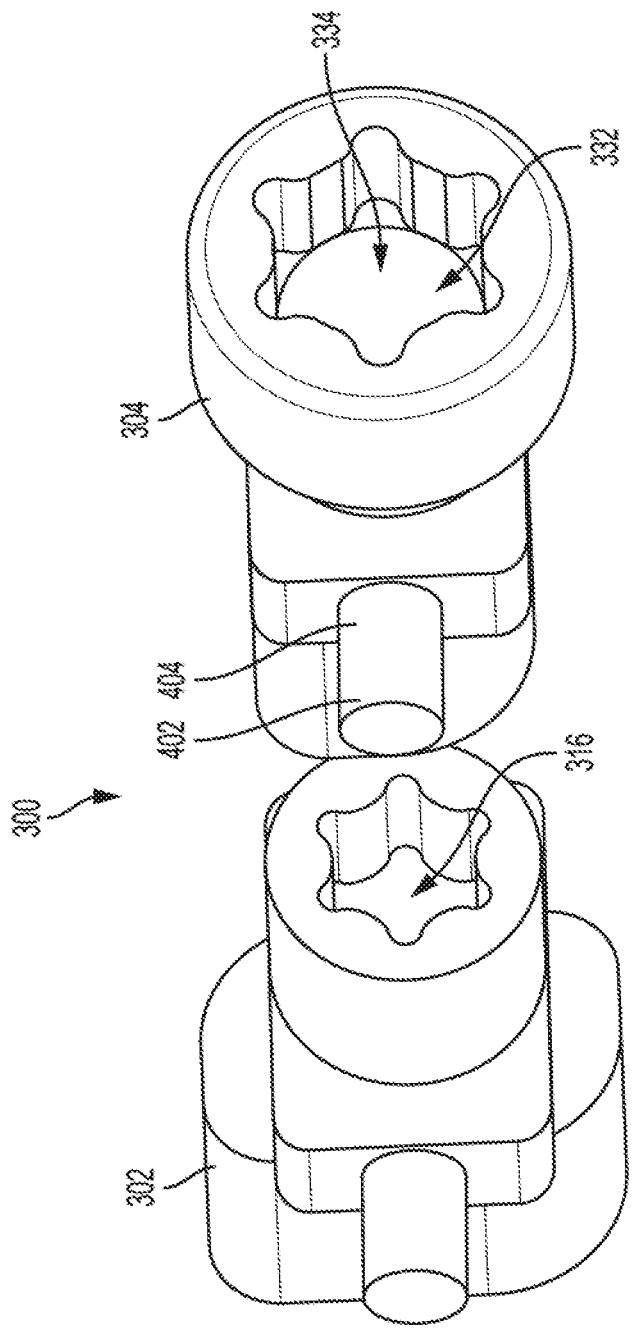
FIG. 7 is a rear perspective view of the insert of FIG. 5.

The present invention can be understood more readily by reference to the following detailed description, examples, and claims, and their previous and following description. Before the present system, devices, and/or methods are disclosed and described, it is to be understood that this invention is not limited to the specific systems, devices, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known aspect. Those skilled in the relevant art will recognize that many changes can be made to the aspects described, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used herein, the singular forms "a," "an" and "the" include plural referents unless the context clearly dictates otherwise. Thus, for example, reference to a "plate" includes aspects having two or more plates unless the context clearly indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

Terms used herein, such as "exemplary" or "exemplified," are not meant to show preference, but rather to explain that the aspect discussed thereafter is merely one example of the aspect presented.

Additionally, as used herein, relative terms, such as "substantially", "generally", "approximately", and the like, are utilized herein to represent an inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

In one aspect, presented herein is an inter-body fusion device for use in spinal surgery, such as, but not limited to, ALIF, OLIF, TLIF, LLIF, PLIF, and DLIF procedures. In another aspect, the inter-body fusion device can be an expandable inter-body fusion device such that a height of the device can be selectively adjusted by a user, such as a surgeon. In a further aspect, the inter-body fusion device can be an adjustable fusion device such that a device angle formed between an upper bone contact surface and a lower bone contact surface is selectively adjustable by the user. In another aspect, the inter-body fusion device can be an expandable, adjustable inter-body fusion device having a selectively expandable height and a selectively adjustable device angle.

In one aspect and as illustrated in FIGS. 1-4, the inter-body fusion device 10 comprises a first plate 100, a second plate 200, and an insert 300 positioned substantially therebetween the first plate 100 and the second plate 200. The first plate has a leading edge 102, a trailing edge 104, an upper bone contact surface 110 and an opposed first plate inner surface 120. The second plate 200 has a leading edge 202, a trailing edge 204, a lower bone contact surface 210 and an opposed second plate inner surface 220. In one aspect, the first plate 100, the second plate 200, and/or the insert 300 define an interior cavity 15.

In one aspect, rotating at least a portion of the insert 300 relative to the first plate 100 and the second plate 200 can increase the distance between the first plate relative to the second plate, effectively expanding the inter-body fusion device and increasing the volume of the interior cavity 15. In another aspect, a device angle $\alpha_1$ formed between a longitudinal axis $L_1$ of the first plate 100 and a longitudinal axis $L_2$ of the second plate 200 can be selectively adjusted by a user to vary the volume of the interior cavity and/or better position the device 10 in the disc space. For example, the device angle $\alpha_1$ can be substantially 0 degrees such that the first plate and the second plate are substantially parallel to each other. In other examples, the device angle $\alpha_1$ can be an acute angle of about 1 degree, 2 degrees, 3 degrees, 4 degrees, 5 degrees, 6 degrees, 7 degrees, 8 degrees, 9 degrees, 10 degrees, 11 degrees, 12 degrees, 13 degrees, 14 degrees, 15 degrees, 20 degrees, 25 degrees, 30 degrees, 35 degrees, 40 degrees, 45 degrees or greater than about 45 degrees.

At least one of the first plate 100 and the second plate 200 has at least one longitudinal sidewall 130, 230 extending substantially between the respective inner surface 120, 220 and bone contact surface 110, 210. In one aspect, the at least one longitudinal sidewall 130, 230 comprises a plurality of longitudinal sidewalls. For example, the longitudinal sidewall can comprise two longitudinal sidewalls. In another aspect, the longitudinal sidewall(s) can be positioned substantially near a peripheral edge 132, 232 of the first and/or second plate.

In one aspect, the longitudinal sidewall 130 of the first plate 100 can define at least one slot 134 having a slot axis $L_4$. In another aspect, the at least one slot of the first plate can comprise a plurality of slots, such as, for example and without limitation, a first slot 136 and a second slot 138. In another aspect, the first slot and/or the second slot can be positioned along the slot axis $L_4$ that is substantially transverse to the longitudinal axis $L_1$ of the first plate 100. Optionally, however, the slot axis $L_4$ of the first slot 136 and/or the second slot 138 can be at an acute slot angle relative to the longitudinal axis $L_1$ of the first plate. That is, the slot axis of the first slot and/or the second slot can be at an acute slot angle $\alpha_2$ relative to the longitudinal axis $L_1$ of the first plate. For example, the slot angle $\alpha_2$ can be about 1 degree, 2 degrees, 3 degrees, 4 degrees, 5 degrees, 6 degrees, 7 degrees, 8 degrees, 9 degrees, 10 degrees, 11 degrees, 12 degrees, 13 degrees, 14 degrees, 15 degrees, 20 degrees, 25 degrees, 30 degrees, 35 degrees, 40 degrees, 45 degrees or greater than about 45 degrees. In another aspect, the slot axis $L_4$ of the first slot 136 and the slot axis of the second slot 138 can be substantially parallel to each other. Alternatively, the slot axis of the first slot can be at an angle relative to the slot axis of the second slot. For example, the slot axis $L_4$ of the first slot 136 can be at an acute angle relative to the slot axis of the second slot 138, or the slot axis of the first slot can be substantially transverse to the slot axis of the second slot. The first slot 136 can be sized, shaped and positioned to engage a portion of a first member 302 of the insert 300, and the second slot 138 can be sized, shaped and positioned to engage a portion of a second member 304 of the insert. In a further aspect, the at least one slot 134 can have a slot wall 140.

In one aspect, the longitudinal sidewall 130 of the first plate 100 can have a wall width of a predetermined thickness. In another aspect, the longitudinal sidewall of the first plate can further comprise at least one substantially flat surface 142 that is substantially parallel to the longitudinal axis $L_1$ of the first plate, according to another aspect. Optionally, the longitudinal sidewall 130 of the first plate 100 can comprise an upper flat surface 144 and a lower flat surface 146. In this aspect, the upper flat surface and the lower flat surface can be spaced from each other a predetermined distance that is less than the height of the insert 300. Alternatively, the upper flat surface 144 and the lower flat surface 146 can be spaced from each other a predetermined distance that is greater than or equal to the height of the insert.

In one aspect, the longitudinal sidewall 230 of the second plate 200 can define at least one slot 234 having a slot axis $L_5$. In another aspect, the at least one slot of the second plate can comprise a plurality of slots, such as, for example and without limitation, a first slot 236 and a second slot 238. In another aspect, the first slot and/or the second slot can be positioned along the slot axis $L_5$ that is substantially transverse to the longitudinal axis $L_2$ of the second plate 200. Optionally, the slot axis $L_5$ of the first slot 236 and/or the second slot 238 can be at an acute slot angle relative to the longitudinal axis $L_2$ of the second plate. That is, at the slot axis of the first slot and/or the second slot can be at an acute slot angle $\alpha_3$ relative to the longitudinal axis $L_2$ of the second plate. For example, the slot angle $\alpha_3$ can be about 1 degree, 2 degrees, 3 degrees, 4 degrees, 5 degrees, 6 degrees, 7 degrees, 8 degrees, 9 degrees, 10 degrees, 11 degrees, 12 degrees, 13 degrees, 14 degrees, 15 degrees, 20 degrees, 25 degrees, 30 degrees, 35 degrees, 40 degrees, 45 degrees or greater than about 45 degrees. In another aspect, the slot axis $L_5$ of the first slot 236 and the slot axis of the second slot 238 can be substantially parallel to each other. Alternatively, the slot axis of the first slot can be at an angle relative to the slot axis of the second slot. For example, the slot axis $L_5$ of the first slot 236 can be at an acute angle relative to the slot axis of the second slot 238, or the slot axis of the first slot can be substantially transverse to the slot axis of the second slot. The first slot 236 can be sized, shaped and positioned to engage a portion of the first member 302 of the insert 300, and the second 238 slot can be sized, shaped and positioned to engage a portion of the second member 304 of the insert. In a further aspect, the at least one slot 234 can have a slot wall 240.

In one aspect, the longitudinal sidewall 230 of the second plate 200 can have a wall width of a predetermined thickness. The longitudinal sidewall of the second plate can further comprise at least one substantially flat surface 242 that is substantially parallel to the longitudinal axis $L_2$ of the second plate, according to another aspect. Optionally, the longitudinal sidewall 230 of the second plate 200 can comprise a lower flat surface 244 and an upper flat surface 246. In this aspect, the upper flat surface and the lower flat surface can be spaced from each other a predetermined distance that is less than the height of the insert 300. Alternatively, the lower flat surface 244 and the upper flat surface 246 can be spaced from each other a predetermined distance that is greater than or equal to the height of the insert.

Referring now to FIGS. 5-9, in one exemplified aspect, the insert 300 comprises a first member 302 and a second member 304 positioned along an insert longitudinal axis $L_3$. In one aspect, the first member can be spaced from the second member a predetermined distance. In another aspect, the first member 302 can be physically separate from the second member 304, as in FIG. 5. Optionally, a portion of the first member can be coupled to the second member (as illustrated in FIG. 10).

In one aspect, the first member 302 has a leading edge 306, a trailing edge 308, an upper plate contact surface 310 extending between the leading edge and the trailing edge, and an opposed lower plate contact surface 312 extending between the leading edge 306 and the trailing edge 308. A first sidewall 314 and a second sidewall 315 spaced from the first sidewall can extend substantially between the upper plate contact surface and the opposed lower plate contact surface.

A first bore 316 can be defined in a portion of the first member. In another aspect, at least a portion of the first bore can be threaded. A portion of the first bore 316 can be configured to engage an actuation device, such as a screwdriver and the like so that rotation of the actuation device can rotate a portion of the first member. For example, the first bore can be slotted to engage a regular screwdriver. In another example, the first bore 316 can be shaped to engage a hexagonal driver and the like.

The first member 302 can comprise a first retainer 320, according to one aspect. The first retainer can be configured to couple a portion of the first member 302 to at least one of the first plate 100 and the second plate 200. In another aspect, the first retainer can restrict longitudinal movement of the first member relative to the first plate and the second plate.

Figure 8:
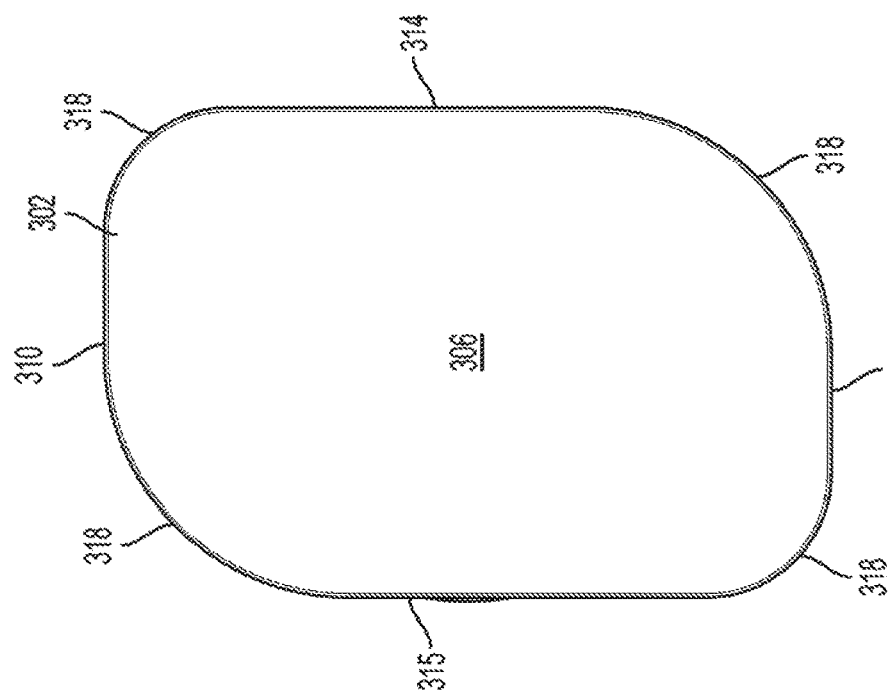
FIG. 8 is front elevational view of the first member of the insert of FIG. 5.

As illustrated in FIG. 8, in one aspect, the upper plate contact surface 310 of the first member 302 can be spaced from the lower plate contact surface 312 a predetermined distance that can be a first member expanded height. In another aspect, the first sidewall 314 can be spaced from the second sidewall 315 a predetermined distance that can be a first member unexpanded height. Optionally, a portion of the upper plate contact surface can be substantially parallel to the lower plate contact surface, and a portion of the first sidewall can be substantially parallel to the second sidewall. As can be appreciated, however, a portion of the upper plate contact surface 310 can be at an acute angle relative to the lower plate contact surface 312, and a portion of the first sidewall 314 can be at an acute angle relative to the second sidewall 315. In another aspect, a portion of the first sidewall and/or the second sidewall can be substantially transverse to the upper plate contact surface 310.

An arcuate transition element 318 can be positioned on or formed along the ends of the sidewalls and the plate contact surfaces of the first member 302. In one aspect, the transition element 318 between the sidewalls 314, 315 and the upper and lower plate contact surfaces can have a predetermined radius. In another aspect, each transition element can have a same radius. Optionally, at least one transition element 318 can have a different radius than another transition element. For example, the transition element positioned between the lower plate contact surface 312 and the first sidewall 314 can have a larger radius than the transition element 318 positioned between the lower plate contact surface 312 and the second sidewall 315. In one aspect, each transition element can have a constant predetermined radius. In another aspect, however, the predetermined radius of each transition element 318 can change as the distance from the sidewalls changes.

With reference again to FIGS. 5-7, the second member 304 has a leading edge 322, a trailing edge 324, an upper plate contact surface 326 extending between the leading edge and the trailing edge and an opposed lower plate contact surface 328 extending between the leading edge 322 and the trailing edge 324. A first sidewall 330 and a second sidewall 331 spaced from the first sidewall can extend substantially between the upper plate contact surface and the opposed lower plate contact surface.

A second bore 332 can be defined in a portion of the second member 304. In one aspect, the second bore can define a longitudinal pathway 334 that extends through the second member 304 so that an actuation device can pass through the longitudinal pathway. A portion or all of the second bore can be threaded. In another aspect, a portion of the second bore 332 can be configured to engage an actuation device, such as a screwdriver and the like so that rotation of the actuation device can rotate a portion of the second member 304. For example, the second bore can be slotted to engage a regular screwdriver. In another example, the second bore 332 can be shaped to engage a hexagonal driver and the like.

The second member 304 can comprise a second retainer 338, according to one aspect. The second retainer can be configured to couple a portion of the second member 304 to at least one of the first plate 100 and the second plate 200. In another aspect, the second retainer can restrict longitudinal movement of the second member relative to the first plate and the second plate.

Figure 9:
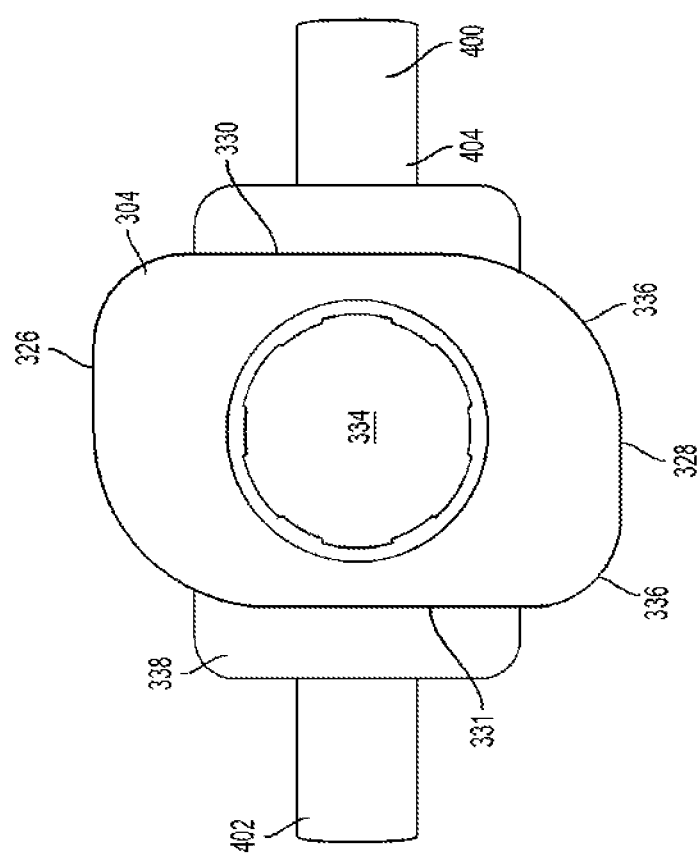
FIG. 9 is a front elevational view of the second member of the insert of FIG. 5.
Figure 10:
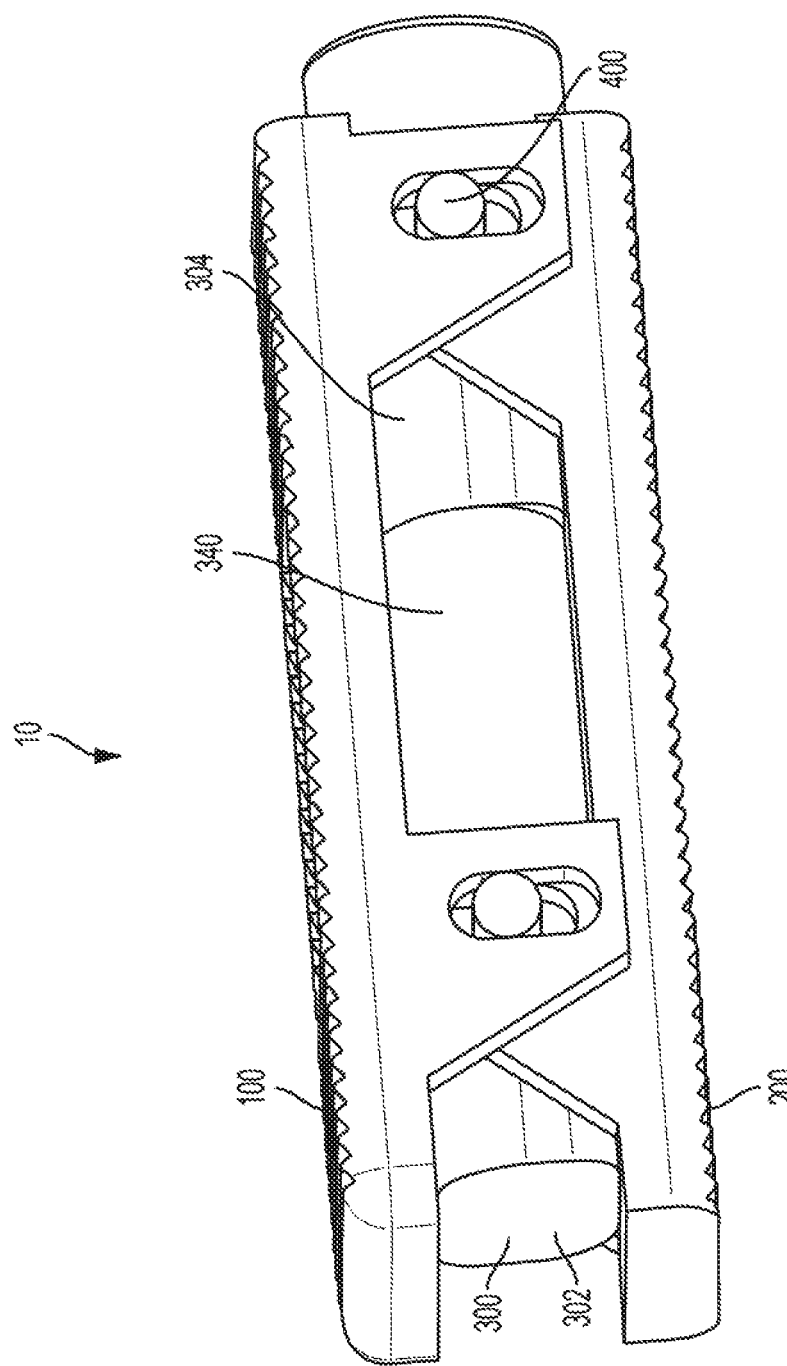
FIG. 10 is a front perspective view of a second embodiment of an expandable, adjustable inter-body fusion device in a first unexpanded position, the device comprising a first plate, a second plate and an insert, according to one aspect.
Figure 11:
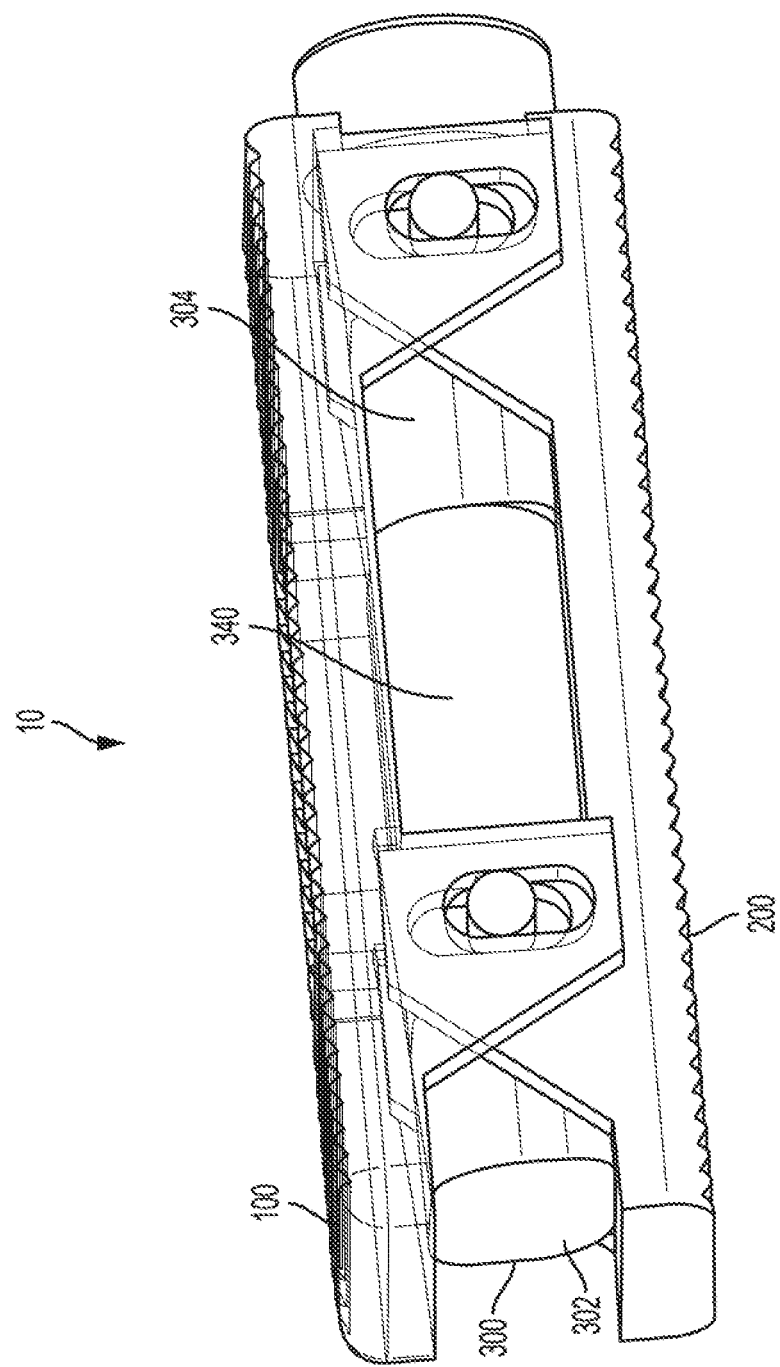
FIG. 11 is a perspective view of the inter-body fusion device of FIG. 10 in the first unexpanded position, in which the first plate is illustrated transparently for clarity.
Figure 12:
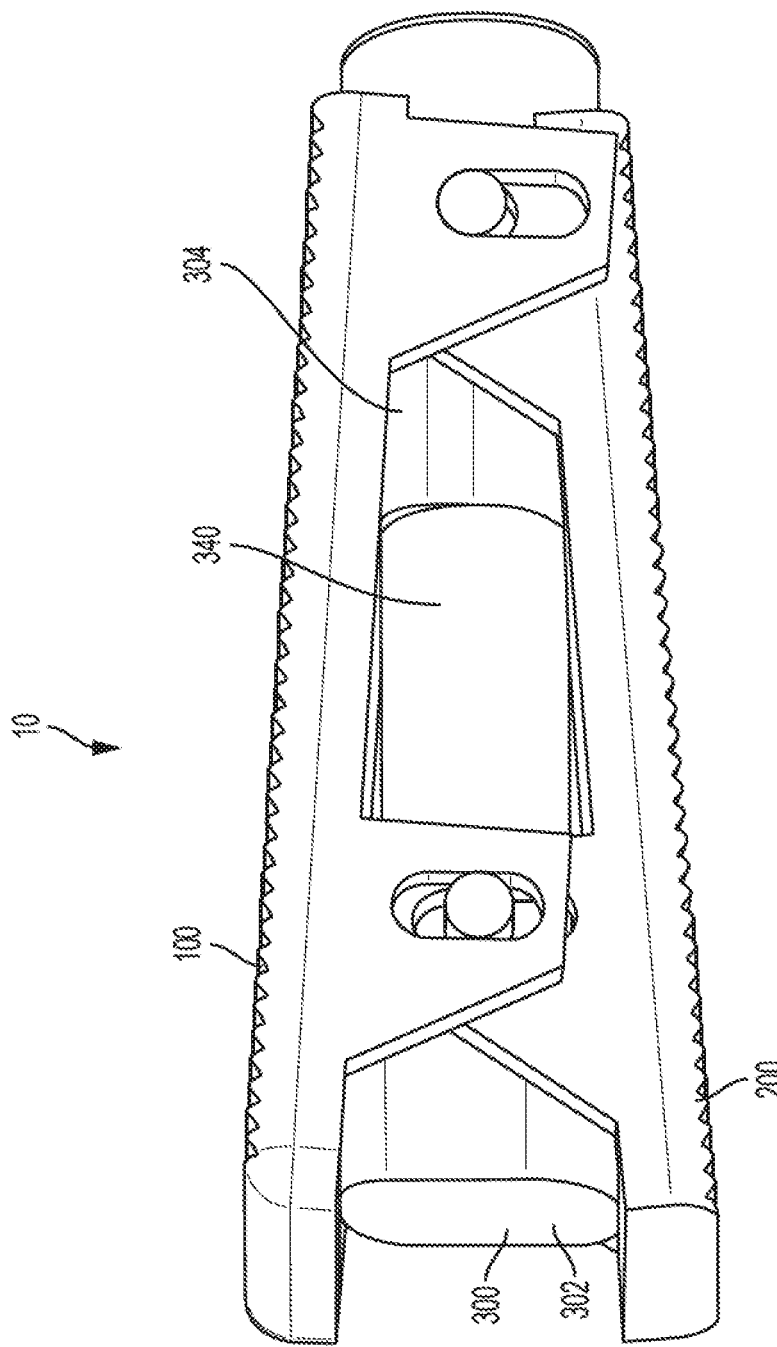
FIG. 12 is a perspective view of the inter-body fusion device of FIG. 10 in which the device angle between the first plate and the second plate is greater than 0 degrees.
Figure 13:
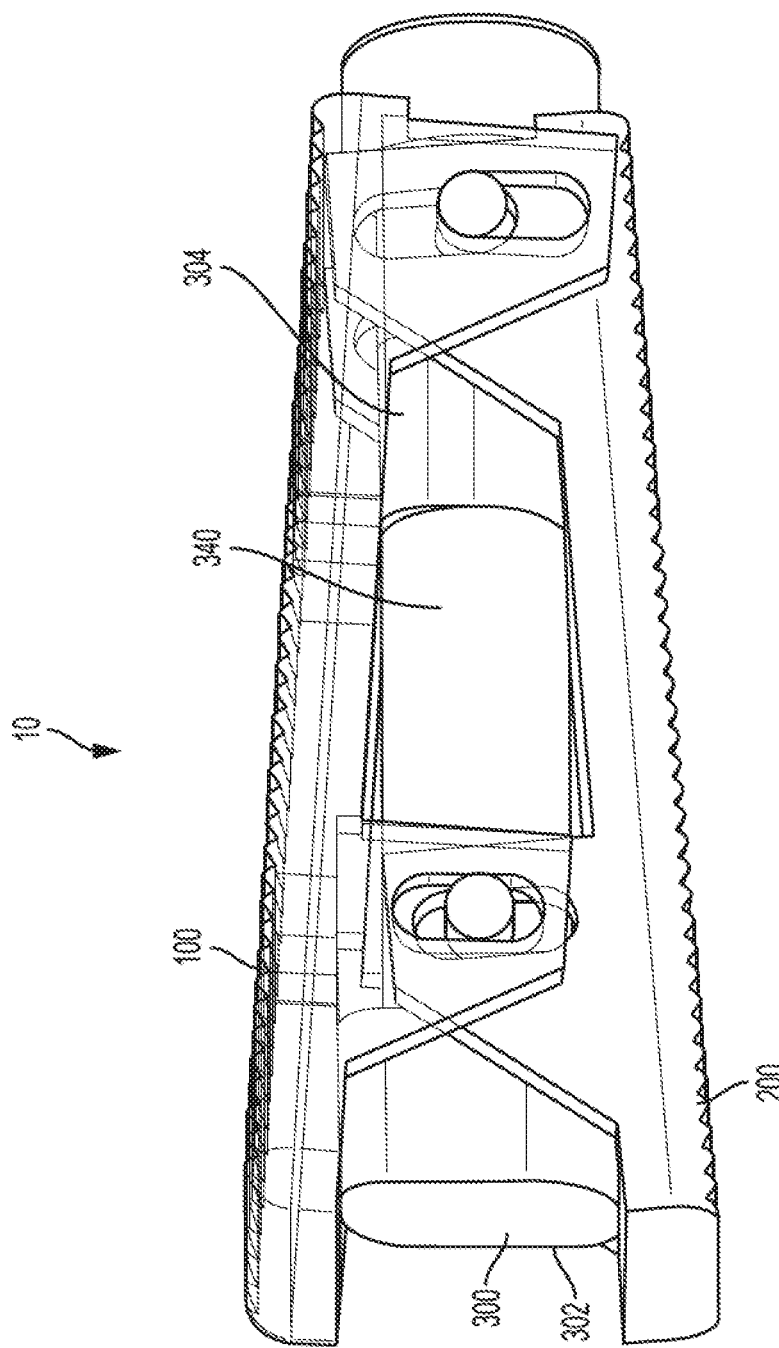
FIG. 13 is a perspective view of the inter-body fusion device of FIG. 10 in in which the device angle between the first plate and the second plate is greater than 0 degrees and in which the first plate is illustrated transparently for clarity.

As illustrated in FIG. 9, in one aspect, the upper plate contact surface 326 of the second member 304 can be spaced from the lower plate contact surface 328 a predetermined distance that can be a second member expanded height. In another aspect, the first sidewall 330 can be spaced from the second sidewall 331 a predetermined distance that can be a second member unexpanded height. Optionally, a portion of the upper plate contact surface can be substantially parallel to the lower plate contact surface, and a portion of the first sidewall can be substantially parallel to the second sidewall. As can be appreciated, however, a portion of the upper plate contact surface 326 can be at an acute angle relative to the lower plate contact surface 328, and a portion of the first sidewall 330 can be at an acute angle relative to the second sidewall 331. In another aspect, a portion of the first sidewall and/or the second sidewall can be substantially transverse to the upper plate contact surface 326.

An arcuate transition element 336 can be positioned on formed along the ends of the sidewalls and the plate contact surfaces of the second member 304. The transition element 336 between the sidewalls 330, 331 and the upper and lower plate contact surfaces 326, 328 can be rounded having a predetermined radius. In one aspect, each transition element can have the same radius. Optionally, at least one transition element 336 can have a different radius than another transition element. For example, the transition element positioned between the lower plate contact surface 328 and the first sidewall 330 can have a larger radius than the transition element 336 positioned between the lower plate contact surface 328 and the second sidewall 331. In one aspect, each transition element can have a constant predetermined radius. In another aspect, however, the predetermined radius of each transition element 336 can change as the distance from the sidewalls changes.

Referring again to FIGS. 1-4, the first retainer 320 and the second retainer 338 can further comprise at least one pin 400 configured to couple a portion of the insert 300 to at least one of the first plate 100 and the second plate 200. For example, a distal end 402 of each pin can be sized and shaped to slidingly engage the slot 134 of the longitudinal sidewall 130 of the first plate and/or the slot 234 of the longitudinal sidewall 230 of the second plate. In this example, a proximal end 404 of each pin can be formed with or securedly attached to a portion of the first or second retainer. In one aspect, at least one pin can be positioned such that a longitudinal axis of the pin is substantially transverse to the longitudinal axis $L_1$ of the first plate 100. As can be appreciated, the at least one pin 400 can comprise a plurality of pins. In one non-limiting example, the device 10 of FIGS. 1-4 comprises 4 pins, though it is of course contemplated that more or less pins can be used. Further, the pins can be placed in other arrangements than those shown.

To assemble the inter-body fusion device 10, the insert 300 can be positioned between the first plate 100 and the second plate 200 such that the leading edge 306 of the first member 302, the leading edge 322 of the second member 304, the leading edge 102 of the first plate, and the leading edge 202 of the second plate are facing the same direction. In one aspect, portions of the first plate 100 can overlie the second plate 200. Correspondingly, in one aspect, each longitudinal sidewall 130 of the first plate 100 can substantially align with a longitudinal sidewall 230 of the second plate 200. For example, each longitudinal sidewall of the first plate can substantially overlie at least a portion of a longitudinal sidewall of the second plate. Optionally, each longitudinal sidewall 130 of the first plate 100 can be positioned adjacent to at least a portion of a longitudinal sidewall 230 of the second plate 200 so that the inner surface 120 of the first plate and the inner surface 220 of the second plate do not contact each other. Portions of the distal end 402 of at least one pin 400 of the first member 302 can be positioned in the first slot 136 of the first plate 100 and the first slot 236 of the second plate 200. Portions of the distal end of at least one pin 400 of the second member 304 can be positioned in the second slot 138 of the first plate 100 and the second slot 238 of the second plate 200.

In use, the inter-body fusion device 10 can be selectively expanded about and between a first, unexpanded position and a second, expanded position. In the first, unexpanded position, the first member 302 and the second member 304 of the insert 300 can be rotated about the insert longitudinal axis $L_3$ to a first insert position. In the first insert position, in one aspect, the first sidewall 314 of the first member 302 can contact and engage a portion of the first plate inner surface 120, and the second sidewall 315 of the first member can contact and engage a portion of the second plate inner surface 220. Optionally, in the first insert position, the first sidewall 314 of the first member 302 can contact and engage a portion of the second plate inner surface 220, and the second sidewall 315 of the first member can contact and engage a portion of the first plate inner surface 120. In another aspect, in the first insert position, the first sidewall 330 of the second member 304 can contact and engage a portion of the first plate inner surface 120, and the second sidewall 331 of the second member 304 can contact and engage a portion of the second plate inner surface 220. Optionally, in the first insert position, the first sidewall 330 of the second member 304 can contact and engage a portion of the second plate inner surface 220, and the second sidewall 331 of the second member 304 can contact and engage a portion of the first plate inner surface 120.

In the second, expanded position, the first member 302 and/or the second member 304 of the insert 300 can be rotated about the insert longitudinal axis $L_3$ to a second insert position. In the second insert position, the upper plate contact surface 310 of the first member 302 can contact and engage a portion of the first plate inner surface 120 of the first plate 100, and the lower plate contact surface 312 of the first member can contact and engage a portion of the second plate inner surface 220 of the second plate 200. Optionally, in the second insert position, the upper plate contact surface 310 of the first member 302 can contact and engage a portion of the second plate inner surface 220, and the lower plate contact surface of the first member can contact and engage a portion of the first plate inner surface 120. In another option, in the second insert position, the upper plate contact surface 326 of the second member 304 can contact and engage a portion of the first plate inner surface 120 of the first plate, and the lower plate contact surface of the second member 304 can contact and engage a portion of the second plate inner surface 220 of the second plate 200. Optionally, in the second, insert position, the upper plate contact surface 326 of the second member 304 can contact and engage a portion of the second plate inner surface 220, and the lower plate contact surface 328 of the second member 304 can contact and engage a portion of the first plate inner surface 120.

Thus, because the first member 302 expanded height is greater than the first member unexpanded height, rotation of the first member from the first insert position to the second insert position cams or urges the first plate 100 away from the second plate 200. Similarly, because the second member 304 expanded height is greater than the second member unexpanded height, rotation of the second member from the first insert position to the second insert position cams or urges the first plate 100 away from the second plate 200.

As can be appreciated, in the second expanded position, the inter-body fusion device 10 can have a height and interior cavity 15 volume that is greater than the height and interior cavity volume of the inter-body fusion device in the first, unexpanded position. That is, in the second expanded position, the first plate inner surface 120 can be spaced therefrom the second plate inner surface 220 a distance greater than in the first, unexpanded position. Thus, in the first unexpanded position, the interior cavity 15 of the device can have a first cavity size, and in the second expanded position the interior cavity can have a second cavity size that is greater than the first cavity size.

In one aspect, in the first, unexpanded position, the longitudinal axis $L_1$ of the first plate 100 and the longitudinal axis $L_2$ of the second plate 200 can be substantially parallel to each other or, optionally, the longitudinal axis $L_1$ of the first plate and the longitudinal axis $L_2$ of the second plate can be at an acute angle relative to each other. In another aspect, in the second, expanded position, the longitudinal axis $L_1$ of the first plate 100 and the longitudinal axis $L_2$ of the second plate 200 can be substantially parallel to each other or, optionally, the longitudinal axis $L_1$ of the first plate and the longitudinal axis $L_2$ of the second plate can be at an acute angle relative to each other.

In order to selectively expand the inter-body fusion device 10 about and between the first unexpanded position and the second expanded position, at least one of the first member 302 or the second member 304 of the insert 300 can be rotated about and between the first insert position and the second insert position. When expanding the inter-body fusion device 10 about and between the first unexpanded position and the second expanded position, the first member 302 and the second member 304 of the insert 300 do not necessarily need be rotated simultaneously or to the same insert position. For example, the first member can be in the first insert position while the second member can be in the second insert position. In another example, the first member 302 can be in the second insert position while the second member 304 can be in the first insert position. Thus, the first member and the second member can be in any insert position between the first insert position and the second insert position at any time regardless of the position of the other member.

As one skilled in the art can appreciate, the amount of separation achievable between the first plate 100 and the second plate 200 can be determined by at least the height of the insert 300. That is, the amount of separation achievable between the first plate and the second plate that can be determined by the first member 302 expanded height and/or the second member 304 expanded height.

It is contemplated that this technology can be used for a variety of implants used for a variety of spinal procedures. As mentioned before, these procedures include, but are not limited to OLIF, DLIF, PLIF, ALIF, TLIF, and LLIF. Because of this, depending upon the procedure and point of insertion for the implant, the geometry of the implant can differ. For example, in a DLIF expandable device, the approach is lateral. As such, the upper bone contact surface 110 can be transversely angled with respect to the lower bone contact surface 210 from a first sidewall to a second sidewall to match, increase, or decrease lordosis.

In an OLIF procedure, the inter-body fusion device 10 can be inserted obliquely, either anteriorly or posteriorly. As such, similar to the DLIF implant, the upper bone contact surface 110 can be angled transversely with respect to the lower bone contact surface 210 from the first sidewall to the second sidewall depending on the need to match, increase, or decrease lordosis. In addition, the upper bone contact surface can also be angled longitudinally with respect to the lower bone contact surface from the leading edge 102 to the trailing edge 104 of the first plate.

In an exemplified aspect, at least one of the first plate 100 and the second plate 200 can define at least one graft window 170, 270 that is in communication with the interior cavity 15. The at least one graft window 170 defined in the first plate can overlie at least a portion of the at least one graft window 270 of the second plate, thereby permitting bone growth therethrough. In another aspect, the upper bone contact surface 110 of the first plate 100 comprises ridges 112 for frictionally engaging a first vertebra of the patient. As can be appreciated, the lower bone contact surface 210 of the second plate can comprise ridges 212 to frictionally engage a second vertebra of the patient.

In one aspect, the inter-body fusion device 10 can be actuated by a device driver. The device driver can comprise a first member driver sized and shaped to engage a portion of the first member 302, and a second member driver sized and shaped to engage a portion of the second member. In another aspect, the first member driver can be a separate tool than the second member driver. Optionally, however, the first member driver and the second member driver can be integrally formed. For example, the device driver can further comprise a handle and a clutch collar that allows the device driver to be adjustable between an engaged position and a disengaged position. In the engaged position, the clutch collar can couple the first member driver to the second member driver so that, upon rotation of the handle, both the first member driver and the second member driver rotate at the same speed as the handle. In the disengaged position, the clutch collar can disengage the first member driver from the second member driver so that upon rotation of the handle, either the first member driver or the second member driver can rotate at the same speed as the handle while the disengaged driver does not rotate.

In use, the first member driver of the actuation device can be inserted through the longitudinal pathway 334 of the second member 304 so that the first member driver can be coupled to the portion of the first bore 316 configured to engage the actuation device. The second member driver can be coupled to the portion of the second bore 332 configured to engage the actuation device. A gripping element of the device driver can grip at least a portion of the inter-body fusion device 10, such as, the first plate 100, the second plate 200, or the insert, such as the second retainer 338 of the insert 300. The clutch collar of the device driver can be placed in the engaged position, and the handle of the device driver can be rotated. For example, if the inter-body fusion device is in the first, unexpanded position, rotation of the handle can cause the first member 302 and the second member 304 of the insert to rotate from the first insert position towards the second insert position. As the first member and the second member rotate towards the second insert position, the first plate 100 and the second plate 200 are urged away from each other, and the height of the device increases. In another example, if the inter-body fusion device is in the second expanded position, rotation of the handle can cause the first member 302 and the second member 304 of the insert to rotate from the second insert position towards the first insert position. As the first member and the second member rotate towards the first insert position, the first plate 100 and the second plate 200 can move towards each other, and the height of the device decreases.

When the desired device height has been reached, the clutch collar can be moved to the disengaged position. In the disengaged position, rotation of the handle can cause only one of the first member 302 and the second member 304 to move. For example, rotation of the handle in a first direction can cause the first member 302 to rotate thereby increasing the angle between the longitudinal axis of the first plate 100 and the second plate 200 (the device angle). In another example, rotation of the first member driver in a second direction that is opposed to the first direction can cause the first member 302 to rotate thereby decreasing the device angle. When the desired device angle has been reached, the device driver can be removed from the device 10.

Figure 14:
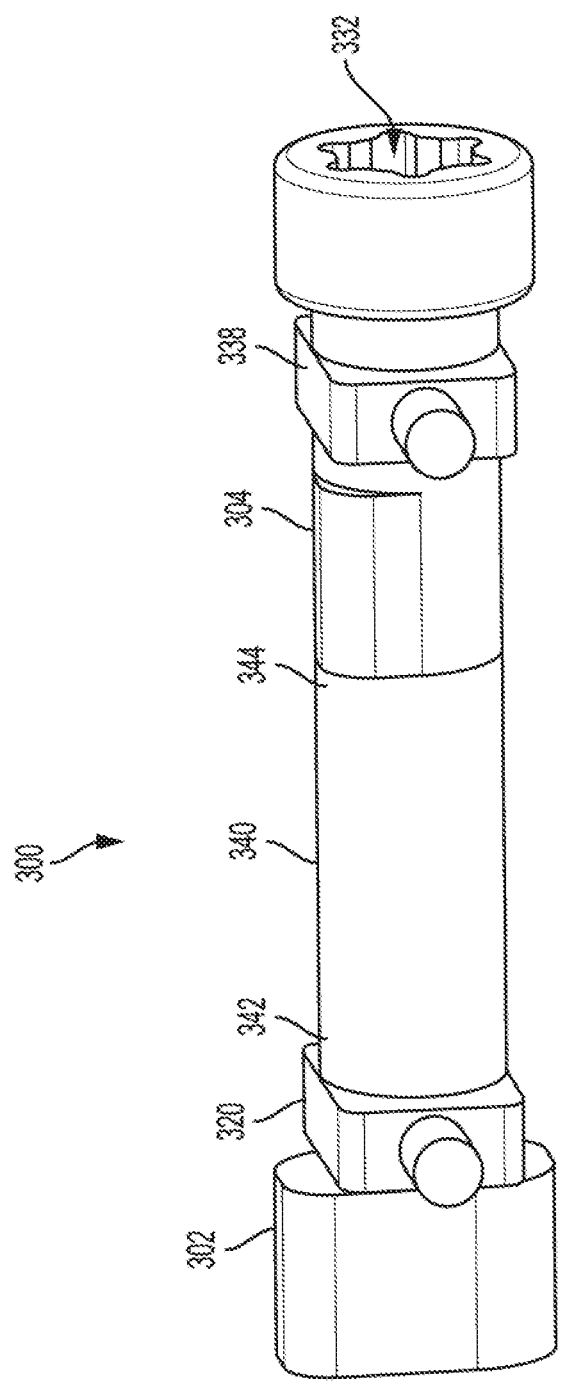
FIG. 14 is a perspective view of the insert of the inter-body fusion device of FIG. 10, according to one aspect.

A second embodiment of the inter-body fusion device 10 is illustrated in FIGS. 10-14, according to one aspect. In this embodiment, the inter-body fusion device can be as described above, comprising a first plate 100, a second plate 200, and an insert 300. Optionally, however, in this embodiment, the insert can be a continuous insert. That is, a portion of the first member 302 of the insert 300 can be coupled to a portion of the second member 304 as illustrated in FIG. 14. In one aspect, the insert 300 can further comprise a coupling shaft 340 configured to couple the first member 302 to a portion of the second member 304. In another aspect, a distal end 342 of the coupling shaft can be coupled to the first member and a proximal end 344 of the coupling shaft 340 can be coupled to the second member. In this aspect, the coupling shaft can be rotated independently of the second member 304 such that the first member 302 can be rotated independently of the second member.

In one aspect, a longitudinal duct 346 can be defined in the coupling shaft so that an actuation device can extend through the longitudinal pathway 334 of the second member 304 and the longitudinal duct 346 of the coupling shaft in order to reach the first member 302. Alternatively, in another aspect, a third bore 348 configured to engage an actuation device can be defined in the proximal end of the coupling. In this aspect, rotation of the coupling shaft by the actuation device can cause the first member to rotate as well.

Assembly of the inter-body fusion device 10 according to this embodiment can be similar to that described above. When adjusting the inter-body fusion device 10 of this embodiment about and between the first unexpanded position and the second expanded position, the first member 302 and the second member 304 of the insert 300 do not necessarily need be moved simultaneously or to the same insert position. For example, the first member can be in the first insert position while the second member can be in the second insert position. In another example, the first member 302 can be in the second insert position while the second member 304 can be in the first insert position. Thus, the first member and the second member can be in any insert position between the first insert position and the second insert position at any time regardless of the position of the other member.

In use, the second member driver can be coupled to the second bore 332 of the second member 304. If the device is in the first, unexpanded position, rotation of the handle can cause the first member and the second member of the insert to rotate from the first insert position towards the second insert position, thereby urging the first plate and second plate away from each other. Upon reaching the desired device height, the second member driver can be removed from the second member, and the first member driver can be inserted through the longitudinal pathway 334 of the second member and optionally through the longitudinal duct 346 of the coupling shaft so that the first member driver can be coupled to the first member 302. Rotation of the first member driver can cause the first member to rotate, thereby changing the angle between the first plate and the second plate (the device angle). For example, rotation of the first member driver in a first direction can cause the first member 302 to rotate in the first direction, thereby increasing the device angle. In another example, rotation of the first member driver in a second direction that is opposed to the first direction can cause the first member 302 to rotate in the second direction, thereby decreasing the device angle. When the desired device angle has been reached, the first member driver can be removed from the device 10.

Also presented herein are methods of using an inter-body fusion device 10 during an inter-body fusion procedure. In one aspect, the method comprises accessing the desired disc space, choosing the inter-body fusion device size with the appropriate height, inserting the inter-body fusion device 10 into the desired area in the disc space, expanding the inter-body fusion device from the first unexpanded position to the second expanded position with longitudinal movement of the insert 300, and adjusting the angle of the of the first plate 100 relative to the second plate. An additional step of packing the interior cavity 15 via the longitudinal pathway 334 of the second member 304 with bone fusion material after expansion is also contemplated. In one aspect, the method of using an inter-body fusion device 10 during an inter-body fusion procedure further comprises the step of securing the insert to the first and second plates. In another aspect, the method of using an inter-body fusion device during an inter-body fusion procedure further comprises the step of securing the inter-body fusion device 10 to the surrounding bony structure.

In one aspect, the step of choosing the inter-body fusion device 10 size with the appropriate height and angle comprises placing an undersized trial device in the disc space, expanding the trial device to the second expanded position, and repeating until the correct height and lordosis is found. The trial height and angle gives the information to prescribe the correct inter-body fusion device for the procedure. In another aspect, the method further comprises selecting a desired embodiment of inter-body fusion device, as described above.

Although several aspects of the invention have been disclosed in the foregoing specification, it is understood by those skilled in the art that many modifications and other aspects of the invention will come to mind to which the invention pertains, having the benefit of the teaching presented in the foregoing description and associated drawings. It is thus understood that the invention is not limited to the specific aspects disclosed hereinabove, and that many modifications and other aspects are intended to be included within the scope of the appended claims. Moreover, although specific terms are employed herein, as well as in the claims that follow, they are used only in a generic and descriptive sense, and not for the purposes of limiting the described invention.

What is claimed is:

1. An expandable inter-body fusion device for use in surgery comprising:
   a first plate having a first plate longitudinal axis, an upper bone contact surface and an opposed first plate inner surface;
   a second plate having a second plate longitudinal axis, a lower bone contact surface and an opposed second plate inner surface, wherein the second plate underlies at least a portion of the first plate; and
   an insert positioned therebetween the first plate and the second plate, wherein the insert has an insert longitudinal axis and comprises a first member and a second member spaced from the first member a predetermined distance, and wherein the first member and the second member are each rotatable about the insert longitudinal axis between a first insert position and a second insert position, and wherein said first member comprises a first retainer configured to couple a portion of the first member to at least one of the first plate and the second plate;
   wherein the device is selectively adjustable about and between a first unexpanded position, in which the first member and the second member of the insert are in the first insert position and a second expanded position, in which at least one of the first member and the second member are in the second insert position, and wherein in the second expanded position, the first plate inner surface is spaced therefrom the second plate inner surface a distance greater than in the first, unexpanded position.

2. The device of claim 1, wherein rotation of at least one of the first member and the second member from the first insert position towards the second insert position comprises at least one of the first member and the second member camming a portion of the first plate away from the second plate.

3. The device of claim 2, wherein each of the first member and the second member of the insert comprise a leading edge, a trailing edge, an upper plate contact surface extending between the leading edge and the trailing edge, an opposed lower plate contact surface extending between the leading edge and the trailing edge, a first sidewall extending between the upper plate contact surface and the opposed lower plate contact surface and a second sidewall opposed to the first sidewall extending between the upper plate contact surface and the opposed lower plate contact surface.

4. The device of claim 3, wherein each of the first member and the second member of the insert further comprise at least one of a first arcuate transition element between the first sidewall and the upper plate contact surface, a second arcuate transition element between the first sidewall and the lower plate contact surface, a third arcuate transition element between the second sidewall and the upper plate contact surface, and a fourth arcuate transition element between the second sidewall and the lower plate contact surface.

5. The device of claim 4, wherein each arcuate transition element has a predetermined radius, and wherein at least one transition element has a different radius than another transition element.

6. The device of claim 3, wherein in the first insert position, the first sidewall of the first member of the insert contacts a portion of the first plate inner surface, and the second sidewall of the first member contacts a portion of the second plate inner surface.

7. The device of claim 6, wherein in the first insert position, the first sidewall of the second member of the insert contacts a portion of the first plate inner surface, and the second sidewall of the second member contacts a portion of the second plate inner surface.

8. The device of claim 7, wherein in the second insert position, the upper plate contact surface of the first member contacts a portion of the first plate inner surface and the lower plate contact surface of the first member contacts a portion of the second plate inner surface.

9. The device of claim 8, wherein in the second insert position, the upper plate contact surface of the second member contacts a portion of the first plate inner surface and the lower plate contact surface of the second member contacts a portion of the second plate inner surface.

10. The device of claim 9, wherein the first member is positionable in the first insert position when the second member is positionable in the second insert position.

11. The device of claim 9, wherein the first member is positionable in the second insert position when the second member is positionable in the first insert position.

12. The device of claim 9, wherein the distance between the upper plate contact surface and the lower plate contact member of the first member is greater than the distance between the first sidewall and the second sidewall of the first member.

13. The device of claim 1, wherein in the first unexpanded position, the first plate longitudinal axis is substantially parallel to the second plate longitudinal axis.

14. The device of claim 13, wherein in the second expanded position, the first plate longitudinal axis is at an acute angle relative to the second plate longitudinal axis.

15. The device of claim 1, wherein the first member is spaced from the second member a predetermined distance and wherein the first retainer comprises at least one pin configured to couple a portion of the first member to at least one of the first plate and the second plate.

16. The device of claim 15, wherein a longitudinal pathway is defined in and extends through the second member.

17. The device of claim 15, wherein a portion of the first member is coupled to the second member.

18. The device of claim 17, wherein the first member and the second member need not necessarily be rotated simultaneously.

19. A method of using an expandable inter-body fusion device during an inter-body fusion procedure, the method comprises:
 accessing a desired disc space in a patient;
 selecting an expandable inter-body fusion device size with an appropriate device height, the device comprising:
  a first plate having a first plate longitudinal axis, an upper bone contact surface and an opposed first plate inner surface;
  a second plate having a second plate longitudinal axis, a lower bone contact surface and an opposed second plate inner surface, wherein the second plate underlies at least a portion of the first plate; and
  an insert positioned therebetween the first plate and the second plate, wherein the insert has an insert longitudinal axis and comprises a first member and a second member spaced from the first member a predetermined distance, and wherein the first member and the second member are each rotatable about the insert longitudinal axis between a first insert position and a second insert position, wherein the first member comprises a first retainer configured to restrict longitudinal movement of the first member relative to the first plate and the second plate;
 inserting the expandable inter-body fusion device into the desired disc space in the patient; and
 expanding the expandable inter-body fusion device from a first unexpanded position to a second expanded position.

20. The method of claim 19, wherein the step of expanding the expandable inter-body fusion device comprises rotating at least one of the first member and the second member about the insert longitudinal axis between the first insert position and the second insert position such that at least one of the first member and the second member cams a portion of the first plate away from the second plate.

21. An expandable inter-body fusion device for use in surgery comprising:
 a first plate having a first plate longitudinal axis, an upper bone contact surface and an opposed first plate inner surface;
 a second plate having a second plate longitudinal axis, a lower bone contact surface and an opposed second plate inner surface, wherein the second plate underlies at least a portion of the first plate such that an interior cavity is defined therebetween the first and second plates; and
 an insert positioned therebetween the first plate and the second plate, wherein the insert has an insert longitudinal axis and comprises a first member and a second member spaced from the first member a predetermined distance, wherein the insert comprises a coupling shaft configured to couple the first member to a portion of the second member, wherein the first member and the second member are each independently rotatable about the insert longitudinal axis between a first insert position and a second insert position, and wherein rotation of at least one of the first member and the second member in a first direction cams a portion of the first plate away from the second plate,
 wherein the device is selectively adjustable about and between a first unexpanded position, in which the first member and the second member of the insert are in the first insert position and a second expanded position, in which at least one of the first member and the second member are in the second insert position, and wherein in the second expanded position, the interior cavity has a second cavity volume that is greater than a first cavity volume of the interior cavity in the first, unexpanded position.

* * * * *